United States Patent
Greco

(10) Patent No.: US 7,126,676 B2
(45) Date of Patent: Oct. 24, 2006

(54) SPECTRAL ANALYSIS OF LIGHT SCATTERED FROM CLOTTING BLOOD

(76) Inventor: Frank Anthony Greco, 250 Grove St., Lexington, MA (US) 02420-1014

( * ) Notice: Subject to any disclaimer, the term of this patent is extended or adjusted under 35 U.S.C. 154(b) by 320 days.

(21) Appl. No.: 10/700,819

(22) Filed: Nov. 4, 2003

(65) Prior Publication Data

US 2004/0090614 A1    May 13, 2004

Related U.S. Application Data

(60) Provisional application No. 60/424,570, filed on Nov. 7, 2002.

(51) Int. Cl.
G01N 33/48    (2006.01)
(52) U.S. Cl. ........................................ 356/39
(58) Field of Classification Search ................ None
See application file for complete search history.

(56) References Cited

U.S. PATENT DOCUMENTS

| | | | | |
|---|---|---|---|---|
| 4,252,536 A | * | 2/1981 | Kishimoto et al. | 356/39 |
| 4,777,141 A | * | 10/1988 | Calzi et al. | 436/69 |
| 4,849,340 A | * | 7/1989 | Oberhardt | 435/13 |
| 6,030,768 A | | 2/2000 | Greco et al. | |
| 6,084,660 A | * | 7/2000 | Shartle | 356/39 |
| 6,099,740 A | * | 8/2000 | Holm et al. | 210/745 |

OTHER PUBLICATIONS

Iwasaka et al., Aggregation of blood platelets in static magnetic fields, Sep. 2000, Magnetics IEEE Transactions, vol. 36 Issue 5 Part 1, pp. 3721-3723.*
Kim et al., Determination of Blood Clot Composition In Real-Time By Laser Scattering Method, Sep. 1995, Engineering in Medicine and Biology Society IEEE 17th Annual Conference, vol. 2 20-23, pp. 1677-1678.*
U.S. Appl. No. 60/424,570, filed Nov. 7, 2002, Greco, Frank A.
Bombardier et al., N. Eng. J. Med., 2000;343:1520-1528.
Mukherjee et al., JAMA 2001;286:954-959.
Greco et al. Arch. Path. Lab. Med. 2000;124:1141-1146.
Riha et al. Clin. Hemorheol. Microcirc. 1997;17:341-346.
Donner et al. Biorheology 1988; 25:367-375.

* cited by examiner

Primary Examiner—Layla G. Lauchman
Assistant Examiner—Juan D. Valentin, II

(57) ABSTRACT

A method for studying whole blood clotting that includes irradiating a specimen with light and recording light reflected into the hemisphere of the irradiating beam. The time course of reflected light intensity is divided into distinct regions, each of which is fit with a mathematical formula. The parameters from these formulas are used to assign values to each specimen. The assigned values identify disease states and quantify the effects of drugs on clotting.

10 Claims, 5 Drawing Sheets

SPECTRAL ANALYSIS OF LIGHT SCATTERED FROM CLOTTING BLOOD

CROSS REFERENCES

The instant application incorporates the following:
Non-provisional Application No. 60/424,570, filed Nov. 7, 2002
Disclosure Document No. 483122, filed Nov. 20, 2000

FEDERALLY SPONSORED RESEARCH

This invention was not made by an agency of the U.S. government nor under any contract with the U.S. government.

BACKGROUND OF THE INVENTION

Field of the Invention: The present invention is an optical method for use in the field of blood clotting, in particular for the study of drug effects on clotting, the detection of clotting abnormalities, and other disease states.

The proper clotting of blood is clearly essential to health. Although insufficient clotting that leads to bleeding is a serious problem for some individuals, an increased tendency to clot that results in stroke, myocardial infarction, or deep vein thrombosis affects a vastly greater number of people. To ward off these thrombotic events, many people take a daily dose of aspirin. Multiple strokes can cause dementia, usually called vascular dementia in this case. The more common form of dementia, Alzheimer's disease, has some points of overlap with vascular disease. For example, certain types of cholesterol-carrying proteins can increase the risk of both myocardial infarction and Alzheimer's disease. Furthermore, people who take ibuprofen have a lower risk of developing Alzheimer's disease than those who do not.

Ibuprofen and aspirin are both members of the same family of drugs, namely, non-steroidal anti-inflammatory drugs (NSAIDs). Most NSAIDs block the conversion of arachidonic acid into its active metabolites. There are three major enzymes that convert arachidonic acid: lipoxygenase, cyclooxygenase-1 (COX1), and cyclooxygenase-2 (COX2). The primary effect of aspirin in preventing thrombotic events is through the inhibition of COX1; the effect of ibuprofen in the prevention of Alzheimer's disease probably does not involve any of these three pathways.

NSAIDs are also used to treat various inflammatory conditions, such as arthritis. In order to maximize therapy for these inflammatory conditions without affecting blood clotting, NSAIDs that specifically inhibit COX2 were developed. Rofecoxib and celecoxib are two commonly prescribed COX2-specific inhibitors. Neither rofecoxib nor celecoxib has any effect on clotting as measured by routine techniques, and both may be administered to people taking anticoagulant drugs like warfarin. It was, therefore, surprising when a study comparing rofecoxib and naproxen (another NSAID) reported a higher incidence of thrombotic events in the rofecoxib-treated arm (Bombardier et al., N.Eng.J.Med. 2000;343:1520–1528). One explanation held that naproxen somehow protected against thrombotic events, as does aspirin (Bombardier et al., N.Eng.J.Med. 2000;343: 1520–1528); another explanation is that rofecoxib promoted coagulation (Mukherjee et al., JAMA 2001;286:954–959). Because no routine test of coagulation detects an effect of COX2 inhibitors, there is a need for a method that can show such an effect in order to investigate the reason for the difference between rofecoxib and naproxen.

As mentioned above, there are many points of overlap between Alzheimer's disease and thrombotic vascular disease. Alzheimer's disease involves the abnormal deposition of material in the brain. An important component of this abnormal material consists of fragments of protein cleaved from a larger protein called amyloid-precursor protein (APP). The enzyme which cleaves APP to form these fragments is called γ-secretase; the bulk of the evidence favors γ-secretase as the site of action of ibuprofen in the prevention of Alzheimer's disease. APP is also found in blood platelets and is normally cleaved during blood clotting. The cleavage of APP in platelets is abnormal in patients with Alzheimer's disease. Furthermore, abnormalities in the red cell are found in Alzheimer's disease (Greco et al., Arch. Pathol. Lab. Med. 2000;124:1141–1146). The present invention grew out of attempts to improve the method that used conformational changes in erythrocyte band 3 to diagnose Alzheimer's disease (U.S. Pat. No. 6,030,768). Although numerous abnormalities have been described in platelets and red cells, none is sufficiently powerful to serve as a diagnostic test for Alzheimer's disease. Because Alzheimer's disease has an insidious onset, there is a need for a test that may detect abnormalities in APP cleavage before the onset of dementia. Furthermore, if this test also detected effects of NSAIDs, it would be useful in gauging the response to prophylactic therapy.

Description of Related Art: There are numerous tests to study blood clotting. Many use the time-to-clot as the endpoint and are insensitive to subtle changes in blood, e.g., the Lee-White clotting time, prothrombin time, partial thromboplastin time, bleeding time. The time-to-clot may be measured optically, mechanically, or electrically, which accounts for most of the instrumental differences among the various methods. Levels of individual clotting factors can be measured, but this is usually done to diagnose a deficiency, not as a routine test of clotting.

Many optical techniques have been applied to blood. When applied to coagulation, the decrease in light transmission as platelet-poor plasma clots is often used. In studying the function of isolated platelets, light scattered at 90° is measured in response to divers agents. As mentioned above, none of these methods can detect an effect of COX2 inhibitors on clotting.

Description of Prior Art Optical: techniques have also been applied to blood rheology, that is, the flow of blood. There are several methods that monitor optical changes in reflected light at various flow rates as the red cells migrate centrally along the axis of flow. If the anticoagulant is reversed, the increase in viscosity that accompanies coagulation may be tracked (Riha et al., Clin. Hemorheol. Mircocirc. 1997;17:341–346). In one special case, the optical changes that accompany clotting resemble those of the present invention (See FIG. 2, Riha et al., Clin. Hemorheol. Mircocirc. 1997;17:341–346). The features of the present invention that distinguish it from and improve upon the rheological technique are discussed in the DETAILED DESCRIPTION OF THE INVENTION. Briefly, the present invention differs from the rheological technique in being stationary, in its method of analysis, and use of broadband illumination.

BRIEF SUMMARY OF THE INVENTION

The invention consists of a device for measuring light reflected from blood as it clots and a method for analyzing the time course to assign parameters to each specimen. Native whole blood, recalcified citrated blood, and isolated blood components may be studied. The invention reveals unique phenomena of blood clotting. It discerns an effect of COX2-specific inhibitors on clotting and is the only method to do so. The COX2 effect is distinct from that of aspirin and naproxen. Therefore, this method may elucidate the mechanism of the higher incidence of thrombotic events in the study comparing rofecoxib and naproxen. Furthermore, the method detects an abnormality in Alzheimer's disease. This method has the potential to become a test for Alzheimer's disease. Moreover, it may be useful in gauging the response of patients taking NSAIDs to prevent either Alzheimer's or thrombotic disease and in the development of prophylactic drugs.

BRIEF DESCRIPTION OF THE DRAWINGS

For a better understanding of the present invention, reference is made to the accompanying drawings, which are incorporated by reference.

DETAILED DESCRIPTION OF THE INVENTION

The invention consists of a device to measure light scattered from whole blood as it clots and a method of analysis to assign numerical values to individual blood samples.

Description of the Device: The device consists of an optical cuvette thermostatted at a temperature from 0–37° C.; the cuvette may be made of glass or polystyrene. It is illuminated by light between 200 and 900 nm. The illumination may be either monochromatic or polychromatic. A photo-detector is placed to measure light scattered between 0 and 90 degrees with respect to the incident beam. In one embodiment of the invention, a glass cuvette was thermostatted at 25° C. and illuminated with 470 nm monochromatic light; a photo-multiplier tube measured the intensity of light scattered at 25°. In a preferred embodiment of the invention, the entire spectral output of a 100 W tungsten lamp illuminated the specimen in a glass cuvette thermostatted at 37° C. A six-around-one fiber-optic probe was used; six optical fibers arranged circumferentially illuminated the specimen, and one central read fiber carried the scattered light to a charge-coupled device array spectrometer (USB2000, Ocean Optics, Dundee, Fla.). This arrangement allowed 1980 wavelengths of the spectrum to be measured at once. Typically, 2–3 spectra per second are collected. The probe containing these seven fibers was oriented at a 45° angle to the surface of the cuvette.

Figure 1A:
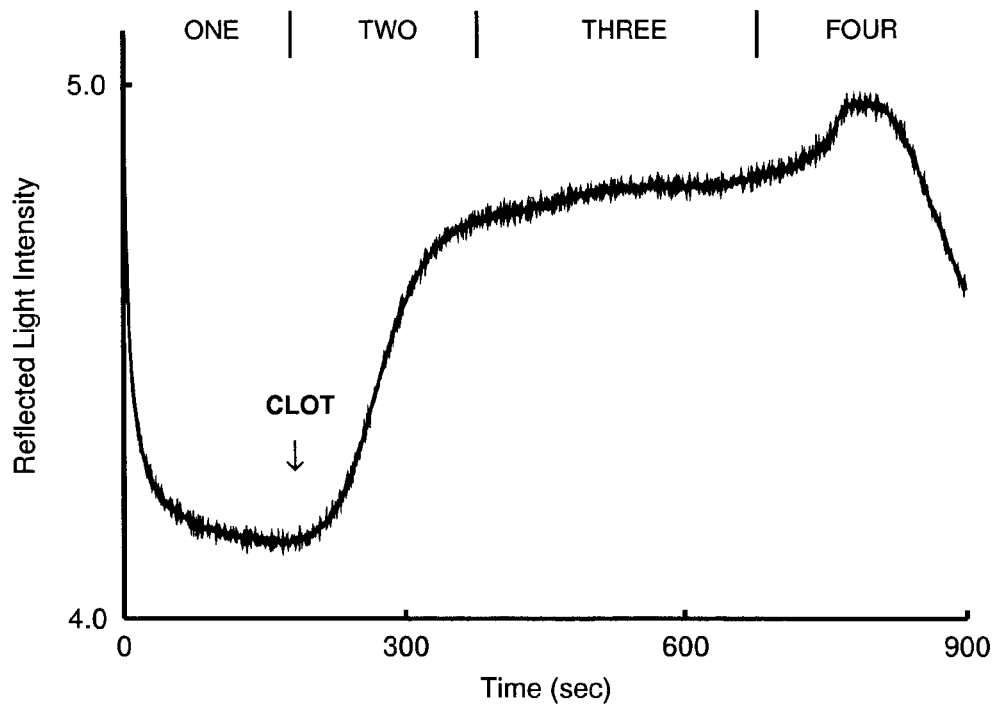
FIG. 1A shows the time course of total light intensity from native whole blood as it clots.
Figure 1B:
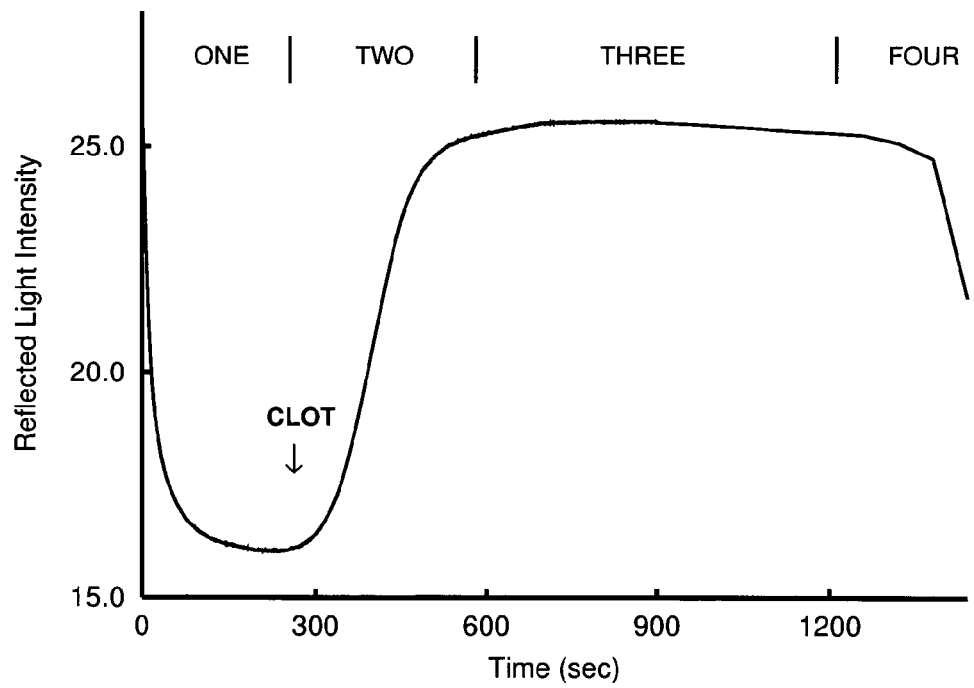
FIG. 1B is the time course of total light intensity from recalcified citrated blood as it clots.

Description of the Specimen: The specimen studied may be whole blood or blood components. In one embodiment of the invention, blood may be drawn into a tube without anticoagulant and immediately transferred to the cuvette; the cuvette surface activates clotting, and the scattered light, either one wavelength or the entire spectrum, is recorded by the devices described above. FIG. 1A shows the time course of total light intensity (broadband) reflected from blood collected in the above manner; the ordinate is the raw output of the spectrometer. Alternatively, blood may be drawn into tubes with an anticoagulant. If the anticoagulant is either sodium citrate or edetic acid, blood is recalcified for the second measurement and clots in the cuvette. In a preferred embodiment of the invention, 1.8% calcium chloride is used to recalcify the specimen (1:10 vol/vol) and to initiate clotting. FIG. 1B shows the time course of total light intensity reflected from recalcified citrated whole blood; the ordinate is the raw output of the spectrometer. In other embodiments of the invention, platelet-poor plasma, platelet-rich plasma, and isolated red cells were studied. Because the surface of the cuvette activates the clotting system, the surface-to-volume ratio must remain constant across measurements. In one embodiment of the method, 1 ml of whole blood was placed in a glass cuvette with dimensions 1 cm by 1 cm by 3 cm.

Description of the Method of Analysis: Analysis begins with the recognition of four regions of the time course: a monotonic decrease, a sigmoidal increase, a linear region, and a terminal phase. FIGS. 1A and 1B show that the same four regions occur in both native and citrated blood. Clot formation as determined by tube inversion occurs at the transition between the first and second regions. The terminal phase (FOUR in FIGS. 1A and 1B) corresponds to clot retraction. It is not observed in all specimens and will not be discussed further here. The other three regions are treated as independent clotting processes and are analyzed independently as described below.

Figure 2:
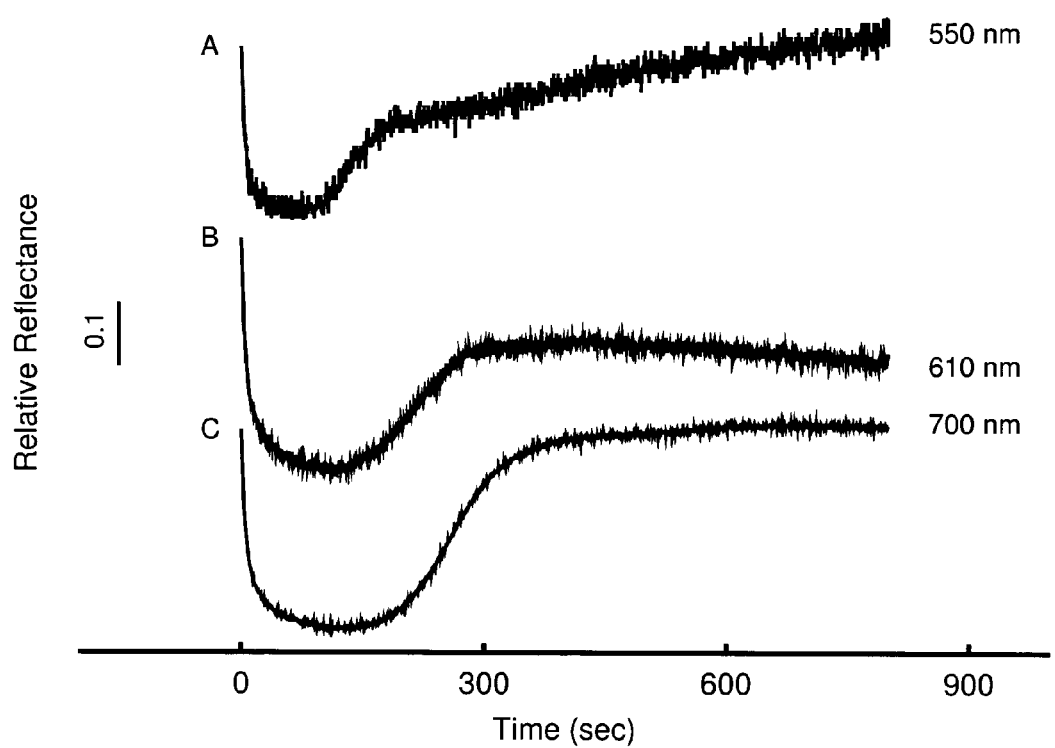
FIG. 2 shows the time course of relative reflectance at selected wavelengths when the light reflected from clotting native blood is dispersed into its spectrum.

Reflectance spectra are reported relative to a reference whose spectral characteristics are independent of time:

$$R(\lambda, t) = \frac{I(\lambda, t)}{I^0(\lambda)} = \frac{C(\lambda, t) - D(\lambda)}{C^0(\lambda) - D(\lambda)}$$

where R is the relative reflectance; $\lambda$ is wavelength; t is time; I is the intensity of reflected light; superscript 0 indicates the reference state; C is the number of photons per second reported by the spectrometer; D is the dark reading from the spectrometer. In a preferred embodiment of the invention, the reference spectrum is calculated by linear extrapolation to t=0 from the first five points of the time course at each wavelength. FIG. 2 shows the time course of relative reflectance from clotting native blood at three selected wavelengths; the terminal phase has been omitted. In normal subjects, the same regions identified in FIG. 1 can be found in the time course at each wavelength.

Each region of the time course is fit mathematically using the method of non-linear least squares. In the preferred embodiment of the invention, the equations used are as follows: monotonic decrease $$R_\lambda(t) = a_1 e^{-k_1 t} + a_2 e^{-k_2 t} + c \tag{1}$$

sigmoidal increase $$R_\lambda(t) = \frac{A}{1 + B\rho^t} + C \quad (2)$$

linear region $$R_\lambda(t) = mt + b \quad (3)$$

This analysis generates eleven parameters at each wavelength. Given that the spectrometer reports intensities at 1980 wavelengths, in principle 21,780 parameters may be calculated for each specimen. In practice, the parameter B of the logistic equation (Eq. 2) has been of particular interest at a few selected wavelengths.

Using the invention:

1. The investigation of blood clotting

Figure 3:
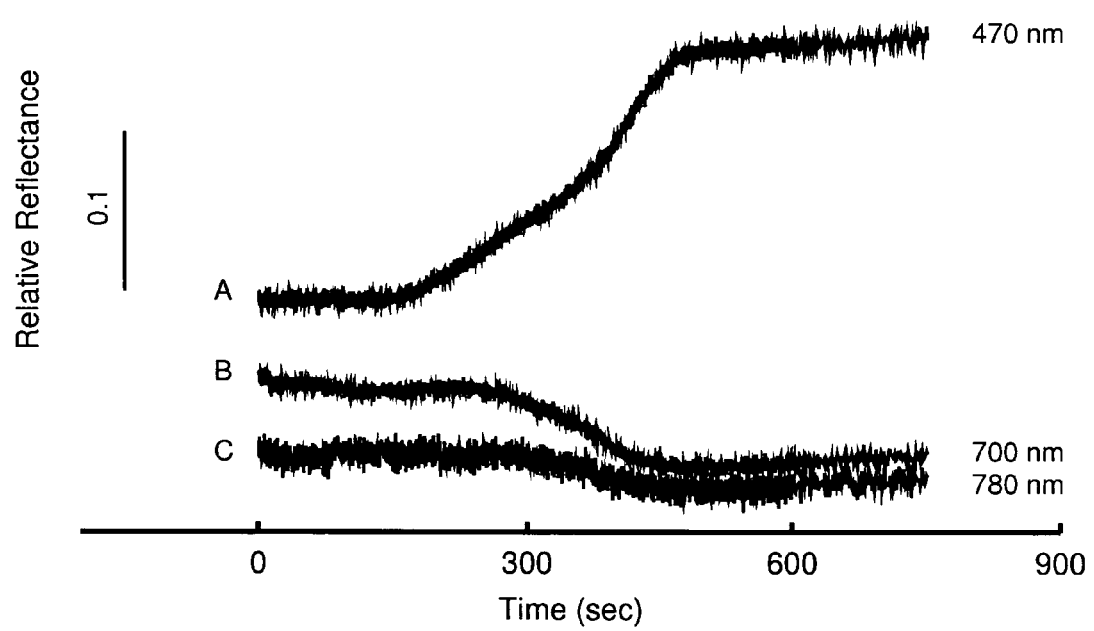
FIG. 3 is the time course of relative reflectance at selected wavelengths when light reflected from clotting platelet-rich plasm is dispersed into its spectrum.

Although the three waveforms in FIG. 2 demonstrate the same regions as shown in FIG. 1, dispersing the reflected light into its spectrum reveals that the sigmoidal increase occurs at different times depending upon the wavelength. If only one biochemical process manifested itself as the sigmoidal increase, the timing would be uniform at all wavelengths. Hence, the sigmoidal increase follows different biochemical processes at different wavelengths. FIG. 3 shows the time course of relative reflectance from recalcified platelet-rich plasma at selected wavelengths; platelet-rich plasma contains all the components of whole blood except red blood cells. The intensity of reflected light increases during coagulation at 550 nm (Waveform A) but decreases during coagulation at 700 nm (Waveform B) and 780 nm (Waveform C). In other words, at shorter wavelengths platelet-rich plasma becomes more back-scattering as it clots; at longer wavelengths platelet-rich plasma becomes more forward-scattering as it clots. The transition occurs around 600 nm and the timing of the change is otherwise identical at all wavelengths (data not shown). It follows that the increase in back-scattered light observed at 700 nm (FIG. 2) and 780 nm (FIG. 2 in Riha et al., Clin. Hemorheol. Mircocirc. 1997;17:341–346) as whole blood clots can not be due to changes in the components of platelet-rich plasma but must be caused by changes in the only missing component: red blood cells. This is a new phenomenon, not revealed by any other method.

The features of the present invention that distinguish it from and improve upon the rheological technique can now be succinctly stated:

(a) Even though the waveforms recorded by the rheological technique under special circumstances resemble those of the present invention, the method of analysis of the rheological technique can not be applied to those special cases. The rheological method of analysis involves a series of measurements in which various shearing forces are applied to a liquid blood sample and then abruptly stopped (Donner et al., Biorheology 1988;25:367–375). The time course of reflected light at one wavelength (780 nm) is monitored; various parameters are calculated from it and assigned as measures to the specimen. This method of analysis can not be applied to clotting blood, the special case in which the waveforms resemble those of the present invention. Hence, the rheological technique can not assign values to clotting blood specimens. The present invention is designed to study clotting blood, and the method of analysis allows values to be determined for each specimen.

(b) The method of analysis of the rheological technique is based on the interpretation of the mechanism underlying the time course of reflected light intensity: rouleaux formation. This interpretation could only be applied to the region of the time course before clot formation. Therefore, even if a scheme for assigning Theological values to clotting specimens could be contrived, it could not analyze the entire time course as does the present invention.

(c) The rheological technique used only a single wavelength (780 nm) and therefore could not detect the variation in the timing of the sigmoidal increase (FIG. 2). The rheological technique could not have discovered the involvement of red cells in the sigmoidal increase above 600 nm. The utilization of broadband illumination distinguishes the present invention.

(d) As a result of the limitations above, the interpretation that the rheological technique gives to the sigmoidal increase is incorrect. Riha et al. explained the increase in back-scattered light intensity at 780 nm as follows: "The intensity of light increases due to formation of a clot with a dense and more light backscattering structure than only aggregated RBC [red blood cells]." (Riha et al., Clin. Hemorheol. Mircocirc. 1997;17:344–345). FIG. 2 and FIG. 3 demonstrate that this explanation can not be true.

Therefore, the invention contributes new insights into blood clotting, improving upon earlier methods; the method of analysis and the use of broadband illumination are essential to these contributions.

2. The study of drug effects on clotting

As mentioned above, the ability of drugs to modify the clotting system can have a tremendous impact on public health, either by preventing stroke, myocardial infarction and deep vein thrombosis or by exacerbating these conditions as an adverse effect. No routine clotting method can detect an effect of COX2 specific inhibitors, yet one report indicated a high incidence of thrombotic events in the group treated with a COX2 specific inhibitor. The invention not only shows an effect of COX2 specific inhibitors but also reveals that at least two different sites may be involved. The table below records results from three experiments done on the same subject. In each measurement, blood was drawn before and two hours after ingesting the drug indicated. The embodiment of the invention used was native whole blood, the preferred configuration of the device, and the preferred method of analysis. Because a red cell process contributes to the sigmoidal increase above 600 nm, four months elapsed between each experiment without ingestion of any drug in order that the red cells would completely turn over. The parameter B calculated from Eq. 2 showed the most variation, and it is reported as a ratio of the value after ingestion to that calculated before ingestion.

Ratio of Post-treatment to Pre-treatment Value of Logistic Parameter B

| Wavelength (nm) | Treatment (single dose) | | |
|---|---|---|---|
| | Aspirin (325 mg) | Celecoxib (400 mg) | Naproxen (600 mg) |
| 470 | 4.48 | 0.087 | 1.63 |
| 550 | 1.45 | 0.154 | 0.03 |
| 610 | 2.18 | 0.055 | 0.34 |
| 700 | 1.85 | 0.107 | 0.28 |

Celecoxib is a COX2-specific inhibitor; it not only has an effect as determined by the invention, but its effect is opposite to that of aspirin. Naproxen has an aspirin-like effect at 470 nm but a celecoxib-like effect at the other wavelengths, which means that at least two sites must be involved. No other method has revealed these facts; spectral analysis of reflected light and the method of calculating parameters are essential.

3. The study of Alzheimer's disease

Figure 4:
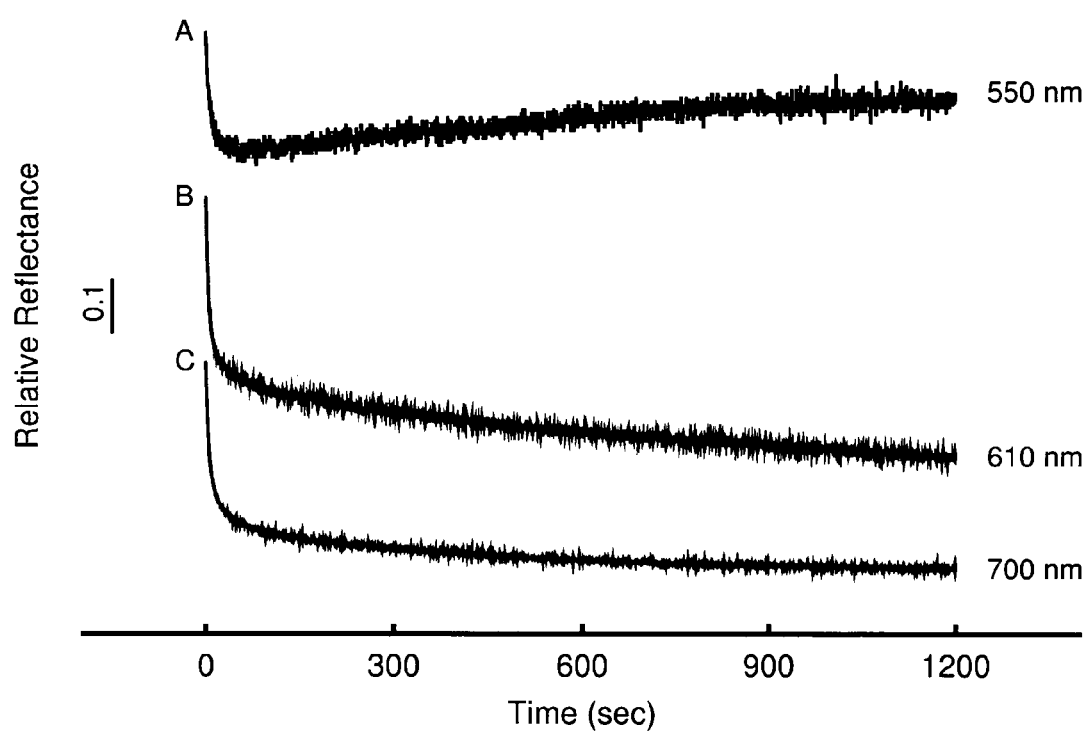
FIG. 4 shows the time course of relative reflectance at selected wavelengths when light reflected from clotting native blood of a patient with Alzheimer's disease is dispersed into its spectrum.
Figure 5:
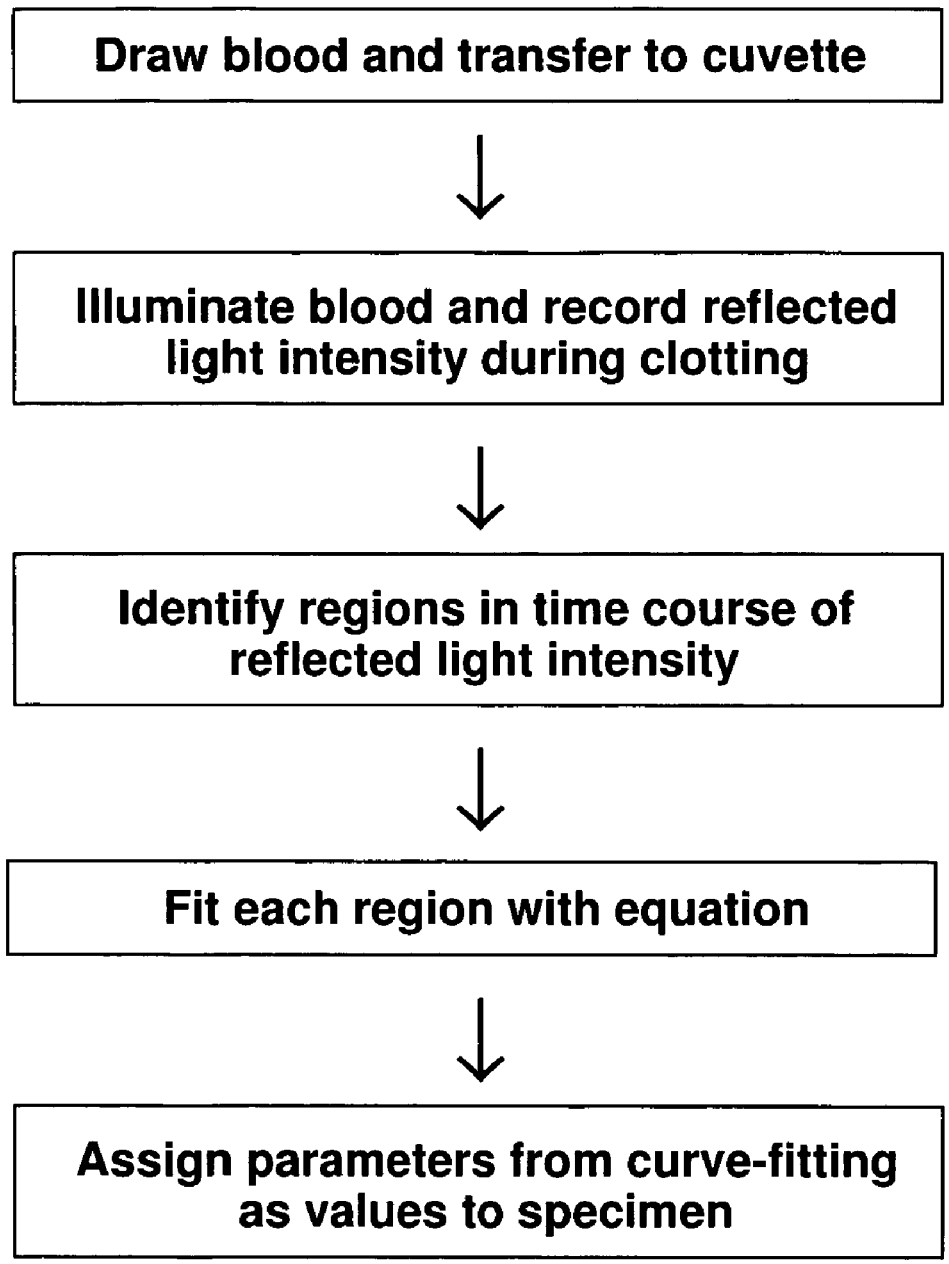
FIG. 5 is a block diagram of the invention.

Specimens from more than fifty individuals have been tested by the invention, and for all non-demented individuals the waveforms resembled those in FIG. 2. Waveforms from a patient with Alzheimer's disease are shown in FIG. 4 and were obtained by the preferred configuration of the invention using native whole blood. At 550 nm the same regions appear as in FIG. 2, although the sigmoidal increase is prolonged. Above 600 nm there is no sigmoidal increase. This feature may be used to detect the pathologic changes of Alzheimer's disease and hence to diagnose it. Furthermore, because the specimen clotted, FIG. 4 supplies further evidence that the sigmoidal increase at wavelengths greater than 600 nm does not result from light back-scattered by the clot, contrary to the proposal of Riha et al. (Riha et al., Clin. Hemorheol. Mircocirc. 1997;17:341–346). Taken together, FIGS. 2, 3, and 4 imply that one defect detected by the invention in Alzheimer's disease is the abnormal absence of the red cell process shown in FIG. 2 at 610 nm (Waveform B) and 700 nm (Waveform C). Spectral analysis is essential to define this defect.

What I claim as my invention is:

1. A method for studying whole blood clotting comprising the following steps: irradiating a clotting specimen with a beam of light and measuring a time course of intensity of the light reflected from the clotting specimen; dividing the time course of reflected light intensity into distinct regions; fitting each region with an appropriate mathematical formula in order to obtain parameters; using the parameters obtained from curve fitting to assign values to that specimen.

2. The method as claimed in claim 1 wherein monochromatic light is used to irradiate the specimen.

3. The method as claimed in claim 1 wherein broadband light is used to irradiate the specimen.

4. The method as claimed in claim 3 wherein the reflected light is dispersed into its spectrum, the time course at each wavelength is divided into distinct regions, each region at each wavelength is fit with an appropriate mathematical formula, and the parameters obtained assigned as values for the specimen.

5. The method as claimed in claim 3 wherein three of the regions of the time course correspond to a monotonic decrease, a sigmoidal increase, and a linear region.

6. The method as claimed in claim 3 wherein the monotonic decrease is fit with a double exponential function, the sigmoidal increase is fit with the logistic function, and the linear region is fit with the formula for a straight line.

7. The method as claimed in claim 3 wherein the invention is used to measure the effects of drugs on clotting.

8. The method as claimed in claim 3 wherein the invention is used to measure the effects of non-steroidal anti-inflammatory drugs on clotting.

9. The method as claimed in claim 3 wherein the invention is used to assess clotting as an element of disease.

10. The method as claimed in claim 3 wherein the invention is used to aid in the diagnosis of Alzheimer's disease.

* * * * *